US005874212A

United States Patent [19]
Prockop et al.

[11] Patent Number: 5,874,212
[45] Date of Patent: Feb. 23, 1999

[54] DETECTION OF SINGLE BASE MUTATIONS AND OTHER VARIATIONS IN DOUBLE STRANDED DNA BY CONFORMATION-SENSITIVE GEL ELECTROPHORESIS

[75] Inventors: Darwin J. Prockop; Matthew J. Rock, both of Philadelphia, Pa.; Arupa Ganguly, Voorhees, N.J.

[73] Assignee: Thomas Jefferson University, Philadelphia, Pa.

[21] Appl. No.: 468,551

[22] Filed: Jun. 6, 1995

Related U.S. Application Data

[63] Continuation-in-part of Ser. No. 61,574, May 13, 1993, abandoned.
[51] Int. Cl.$^6$ ............................... C12Q 1/68; C25D 3/62
[52] U.S. Cl. .......................... 435/6; 205/456; 205/461; 205/469; 205/450
[58] Field of Search .................... 435/6; 935/76, 935/77, 78; 205/450, 456, 461, 469

[56] References Cited

U.S. PATENT DOCUMENTS

| | | | |
|---|---|---|---|
| 4,794,075 | 12/1988 | Ford et al. ................................. | 435/6 |
| 4,879,214 | 11/1989 | Kornher et al. ........................... | 435/91 |
| 5,217,863 | 6/1993 | Cotton et al. .............................. | 435/6 |
| 5,545,527 | 8/1996 | Stevens ...................................... | 435/6 |
| 5,633,129 | 5/1997 | Karger et al. .............................. | 435/6 |

OTHER PUBLICATIONS

Bhattacharyya, A. and Lilley, "Single Base Mismatches in DNA Long–and Short–range Structure Probed by Analysis of Axis Trajectory and Local Chemical Reactivity", *J. Mol. Biol.* 1989, 209, 583–597.

Buche et al., "Glycine and Other Amino Compounds Prevent Chromatin Precipitation at Physiological Ionic Strength", *FEBS Letters* 1989, 247(2), 367–370.

Chan, D. and Cole, "Low Basal Transcription of Genes for Tissue–specific Collagens by Fibroblasts and Lymphoblastoid Cells", *The J. of Biol. Chem.* 1991, 266(19), 12487–12494.

Cotton, R., "Detection of Single Base Changes in Nucleic Acids", *Biochem. J.* 1989, 263, 1–10.

Ganguly, A. and Prockop, "Detection of Single–base Mutations by Reaction of DNA Heteroduplexes with a Water-–soluble Carbodiimide Followed by Primer Extension: Application to Products from the Polymerase Chain Reaction", *Nucleic Acids Res.* 1990, 18(13), 3933–3939.

Innis et al., "PCR Protocols", Academic Press, Inc., San Diego, CA 1990.

Kalnick, M. et al., "Conformational Transitions in Cytidine Bulge–Containing Deoxytridecanucleotide Duplexes: Extra Cytidine Equilibrates between Looped Out (Low Temperature) and Stacked (Elevated Temperature) Conformation in Solution", *Biochemistry,* 1989, 28, 294–303.

Lerman, L. and Silverstein, "Computational Simulation of DNA Melting and Its Application to Denaturing Gradient Gel Electrophoresis", *Methods in Enzymology* 1987, 155, 482–501.

Levine, L. et al., "The Relationship of Structure to the Effectiveness of Denaturing Agents for Deoxyribonucleic Acid", *Biochemistry* 1963, 2(1), 168–175.

Melchior, W. and Von Hippel, "Alteration of the Relative Stability of dA.dT and dG.dC Base Pairs in DNA", *PNAS USA* 1973, 70(2), 298–302.

Myers et al., "Detection and Localization of Single Base Changes by Denaturing Gradient Gel Electrophoresis", *Methods in Enzymology* 1987, 155, 501–527.

Orosz, J. and Wetmur, "DNA Melting Temperatures and Renaturation Rates Concentrated Alkylammonium Salt Solutions", *Biopolymers* 1977, 16, 1183–1199.

Sambrook et al., "Molecular Cloning: A Laboratory Manual", Cold Spring Harbor Press, Cold Spring Harbor, NY 1989.

Stratagene 1988 Catalog.

Wang, Y.–H. and Griffith, "Effects of Bulge Composition and Flanking Sequence on the Kinking of DNA by Bulged Bases", *Biochemistry* 1991, 30, 1358–1363.

White, M. et al., "Detecting Single Base Substitutions as Heteroduplex Polymorphisms", *Genomics* 1992, 12, 301–306.

Woodson, S. and Crothers, "Structural Model for an Oligonucleotide Containing a Bulged Guanosine by NMR and Energy Minimization", *Biochemistry* 1988, 27, 3130–3141.

Davis et al. Basic Methods in Molecular Biology, pp. 106–108, Elsevier Publishing, NY (1986).

The Stratagene Catalog p. 39 (1988).

White et al. Genomics 13: 301–306 (1992).

"Nucleic Acid Sequencing", The United States Biochemical Corporation [USB (Apr. 1993).

Lerman et al. Methods in Enzymology 155:482–501 (1987).

*Primary Examiner*—W. Gary Jones
*Assistant Examiner*—Ethan Whisenant
*Attorney, Agent, or Firm*—Panitch Schwarze Jacobs & Nadel, P.C.

[57] ABSTRACT

Simple methods of detecting single base pair mutations and other mutations in nucleic acid sequences are provided comprising generating a sample which may comprise heteroduplexes and homoduplexes and performing gel electrophoresis on the sample. The sample may be analyzed for one or more isolated high-melting domains prior to performance of gel electrophoresis. Kits are also provided.

19 Claims, 5 Drawing Sheets

G/A polymorphism

C/T Polymorphism

Alu I-C/T Polymorphism

DETECTION OF SINGLE BASE MUTATIONS AND OTHER VARIATIONS IN DOUBLE STRANDED DNA BY CONFORMATION-SENSITIVE GEL ELECTROPHORESIS

This application is a CIP of U.S. Ser. No. 08/031,574, filed May 13, 1995, and now abandoned.

GOVERNMENT SUPPORT

This invention was supported in part by the National Institutes of Health Grants AR-38188 and AR-39740. The United States Government may have certain rights in this invention.

FIELD OF INVENTION

The present invention is directed to rapid methods for detection of single-base mutations and other variations in DNA that are of interest as a cause of genetic diseases and in many other fields of medicine and biology.

BACKGROUND OF THE INVENTION

Double strands of deoxyribonucleic acid (DNA) provide the essential information that defines the structure and function of most living organisms. Each strand of DNA is composed of a linear sequence of four nucleotide bases: adenine (A), thymine (T), guanine (G) and cytosine (C). The two strands of double-stranded DNA are complementary so that A pairs with T and pairs G with C. The sequence of bases in specific regions of the DNA are defined as genes since they determine the sequences of amino acids found in specific polypeptide chains of proteins. Other base sequences in the DNA participate in regulation of gene expression in that they play a role in defining when a gene is expressed so that protein is synthesized, and when a gene is not expressed. The differences in the sizes, shapes and other features among different species of organisms is largely explained by differences in the base sequences of their DNA. The DNA from individuals of the same species, however, can also vary in base sequence. Some of the variations in base sequence have little or no consequences, but others have dramatic effects. For example, a change or mutation in one base of the 2,000 or so bases in the sequence of the gene for β-globin results in sickle cell anemia or other serious anemias in man. Single-base mutations or other changes such as deletions or insertion of bases in other genes cause diseases such as cystic fibrosis, Huntingdon's chorea, and osteogenesis imperfecta. For these and related reasons, detecting single-base mutations and other changes in DNA is of great importance for the treatment and diagnosis of diseases in humans, including the possibility of gene therapy. In addition, detection of mutations in genes is of great importance in a variety of other fields such as animal husbandry, development of new plant species and basic research. Ribonucleic acid (RNA) such as mRNA, is also composed of a linear sequence of nucleotide bases, adenine (A), uracil (U), guanine (G) and cytosine (C). Because RNA is derived from coding regions of DNA, mutations of a gene are also reflected in RNA.

Over the past several decades, a series of powerful techniques have been developed to precisely define the base sequences of fragments of DNA. The techniques involve chemical or enzymatic manipulation of the DNA followed by electrophoretic separation of the samples so that the exact sequence of bases in the DNA can be defined. However, defining the exact base sequences of a region of DNA or of a specific gene that may be as large as 200,000 base pairs continues to be a tedious and time-consuming undertaking for a number of reasons. For example, the number of manipulations is very large and for technical reasons, some DNA sequences are difficult to define. In addition, the amount of information that must be processed is very large and, therefore, errors are frequently made. Therefore, there is an important need for alternative procedures whereby short regions or fragments of DNA can be rapidly screened for the presence or absence of single-base mutations and other changes. More specifically, there is a need for methods whereby one can determine whether the base sequence in a test sample of DNA is or is not exactly the same as the base sequence in a second sample of standard DNA which may be the normal, unmutated or wild type DNA.

Analysis of DNA has been greatly facilitated by the development of the polymerase chain reaction (PCR) whereby a short region of approximately 1,000 bp of DNA can be amplified so that adequate amounts of the DNA are available for analysis. In addition, a number of techniques have been developed that can be used to detect single base mutations and other changes in the DNA amplified by the PCR or in DNA obtained by other procedures.

At least four general strategies have been pursued to develop such methods. One general strategy is to use enzymes that cleave DNA at sites in which a base is mismatched. In practice, the procedures involve preparation of heteroduplexes of DNA by first mixing a test DNA with a wild type DNA. The mixed sample is heated under conditions in which the double-stranded DNA will separate into single strands. Thereafter the mixture of single stranded DNA is cooled under conditions in which some single strands re-associate into double-stranded DNA having two completely complementary strands of base pairs (homoduplexes) and some single strands re-associate into double-stranded DNA in which most of the bases are complementary but one or more bases are not (heteroduplexes). An enzyme which recognizes mismatched DNA strands is then incubated with the mixture of DNAs so that it will cleave the heteroduplexes into two or more fragments that can be detected by separating the samples by electrophoresis. A second general strategy to detect mutations in DNA is based upon the principle that double-stranded DNA heteroduplexes will separate into two strands (dehybridize) under milder conditions than will double-stranded DNA homoduplexes. In practice, the principle is usually performed by electrophoresis of the DNA through gels which contain an increasing gradient of temperature or denaturants that promote the separation of double-stranded DNA into single-stranded DNA. Under appropriate conditions, heteroduplexes of DNA will partially separate into single-stranded molecules before homoduplexes of the same DNA. Therefore, the presence of a mutation can be detected by the slower migration in an electric field of heteroduplexes compared to homoduplexes.

A third general strategy is to use chemical methods either to modify unpaired bases or to modify and cleave unpaired bases in DNA heteroduplexes. In one variation of this strategy, heteroduplex DNA is cleaved by a chemical reagent at the site of a mismatch into two or more fragments. In another variation, one or both of the mismatched bases are modified by a chemical reagent that will preferentially modify bases that are not paired with a complementary base, but will not effectively modify bases that are paired with complementary bases in double-stranded DNA. The presence and usually the site of the chemically modified base can then be detected by a variety of techniques familiar to those skilled in the art.

A fourth general strategy is to detect mutations by separating or denaturing double-stranded DNA into single-stranded DNA and then comparing the electrophoretic mobility of the single strands of DNA to single strands of wild type DNA.

A number of variations of these four general strategies have been developed. Most of these strategies have been reviewed by Cotton, (1989) *Biochemical Journal* 263:1–10, and Ganguly and Prockop, (1990) *Nucleic Acids Research* 18:3933–3939. As indicated by Cotton in his review, however, each of the methods has limitations. For example, cleavage of mismatched bases in DNA heteroduplexes with the enzyme S1 nuclease was not sensitive enough to detect some single-base mismatches. Digestion of RNA-RNA heteroduplexes with the enzymes ribonuclease A or T1 was more sensitive but still detected only 60 to 70% of all possible single-base mismatches. Identification of single-base mutations by electrophoresis in denaturing gels was limited to the detection of mutations at low melting domains of DNA fragments and, therefore, required introduction of base sequences of Gs and Cs at one end of the DNA fragments to serve as clamps to delay the separation of the two strands. The technique also required careful optimalization of the conditions for electrophoresis for each DNA fragment. Chemical modification of DNA heteroduplexes with a water-soluble carbodiimide, a reagent that reacts with unpaired Gs and Ts, was shown to modify the electrophoretic behavior of DNA heteroduplexes containing six different single-base mismatches, but the effects on electrophoretic migration were often small and not readily detectable. In a modification of the carbodiimide procedure, antibodies specific for the carbodiimide-modified DNA were used to locate the site of single-base mismatches by immunoelectron microscopy of DNA heteroduplexes. The procedure, however, required time consuming electron microscopy. In still another variation of the carbodiimide technique, primer extension with DNA polymerase was used to locate the site of the mismatched base that was modified by carbodiimide. However, the procedure was time-consuming and required use of radioisotopes. Another chemical method involved modification of unpaired Cs in DNA heteroduplexes with hydroxylamine and unpaired Ts and Cs with osmium tetroxide. The DNA was then cleaved at the modified bases by treatment with piperidine and the resulting fragments were analyzed by gel electrophoresis to detect the site of the mismatch. The procedure was shown to detect mismatched bases in many sequence contexts but required preparation of radioactive probes to detect the cleaved fragments and as well as requiring two separate chemical reactions. At least one report (Bhattacharyya and Lilley, 1989 *Journal of Molecular Biology,* 209:583–593) indicated that the technique did not detect all single base mismatches in some sequence contexts. Detection of mutations by examining the electrophoretic mobility of single-stranded DNA is limited by the fact that the technique will detect mutations only in DNA fragments that are smaller than 300 bp and perhaps smaller than 200 bp. Also, the effect of a mutation on migration of the DNA strands is unpredictable and, therefore, the assays require careful analysis.

More recently, differential electrophoretic migration of homoduplexes and heteroduplexes of double-stranded DNA with single base mismatches has been described. For example, White et al. ( (1992) *Genomics* 12:301–306) report electrophoretic separation of homoduplexes and heteroduplexes of DNA fragments produced by the electrophoresis in polyacrylamide gel. White et al. produced a series of point mutations in a defined region of DNA from the equine infectious anemia virus. Each mutation was a single-base substitution. Eight of nine single-base mutations were detected by electrophoresis of heteroduplexes and homoduplexes of the DNA. It should be noted however, that the DNA sequence chosen by White et al. was a specialized base sequence that formed a hairpin-like structure in the DNA and, therefore, could be expected to be changed more dramatically by the presence of a single-base mismatch than would double-stranded DNA having more common tertiary structure. White et al. did not explore other sequence contexts. Most importantly, electrophoresis conditions for the separation of the homoduplexes and heteroduplexes was a standard buffer such as 25 mM Tris-borate and 1 mM EDTA together with 1% glycerol. In a few experiments mildly denaturing electrophoretic environment was created by adding 5% to 30% urea. White et al. found that 10% urea provided the greatest separation between homoduplexes and heteroduplexes. However, experiments have shown that most single-base mutations in heteroduplexes could not be detected using the method of White et al. Accordingly, there is a long felt need for a rapid, accurate method for detecting single base mutations in nucleic acid sequences. The present invention meets these and other needs which will become apparent through a reading of the following detailed description and accompanying claims.

SUMMARY OF THE INVENTION

The method of the present invention overcomes the limitations of previous methods for the detection of single base and other changes in nucleic acid fragments. Methods of the present invention can be applied directly to nucleic acid fragments obtained from several sources and do not require any special manipulation of the nucleic acid fragments such as a chemical reaction with an enzyme. Moreover, methods of the present invention do not require the use of any toxic reagents or radioactivity. The present invention does not require any specialized apparatus or optimalization of conditions for analysis of different DNA fragments. In accordance with methods of the present invention large numbers of samples can be processed rapidly.

The present invention provides methods for detecting one or more base pair mutations in a nucleic acid sequence by differentiating heteroduplexes from homoduplexes in a sample comprising providing a polyacrylamide gel for gel electrophoresis comprising from about 3% to about 20% polyacrylamide; from about 1% to about 50% of a denaturing component comprising at least one denaturing agent selected from the group consisting of aliphatic alcohols, cyclic alcohols, alicyclic compounds, amides, ureas and carbamates, said denaturing component selected to enhance resolution of homoduplexes and heteroduplexes in said gel; from about 10 to about 100 mM TE buffer; and from about 10 to about 100 mM taurine. Homoduplexes and heteroduplexes are generated in a sample and gel electrophoresis is performed on the sample using said polyacrylamide gel. Heteroduplexes will migrate more slowly in the gel than homoduplexes, allowing differentiation of the duplexes.

The present invention also provides methods for detecting one or more base pair mutations in a nucleic acid sequence by differentiating heteroduplexes from homoduplexes in a sample comprising generating a sample of homoduplexes and analyzing the sample of homoduplexes for at least one isolated high melting domain. Thereafter a polyacrylamide gel is provided for gel electrophoresis comprising from about 3% to about 20% polyacrylamide; from about 1% to about 50% of a denaturing component comprising at least one denaturing agent selected from the group consisting of aliphatic alcohols, cyclic alcohols, alicyclic compounds, amides, ureas and carbamates, said denaturing component selected to enhance resolution of homoduplexes and heteroduplexes in said gel; from about 10 to about 100 mM TE buffer; and from about 10 to about 100 mM taurine, the concentration of said denaturing agent being adjusted to compensate for any isolated high melting domains which are identified. A sample of homoduplexes and heteroduplexes in a sample is generated and gel electrophoresis is performed on the sample using said polyacrylamide gel. Heteroduplexes will migrate more slowly in the gel than homoduplexes.

Diagnostic kits comprising polyacrylamide gels of the present invention and PCR primers for amplification of a desired gene are also provided.

BRIEF DESCRIPTION OF THE FIGURES

FIG. 4 shows three polyacrylamide gels of PCR products from COL7A1 G/A, C/T and AluI-C/T polymorphisms and mutations.

The eukaryotic consensus splice acceptor site sequence is: $(Py)_n NPyAG^{-1} G^{+1}$. The normal splice acceptor site sequence for IVS17 is: ttttcag$^{-1}$ G$^{+1}$GT . . . The mutant splice acceptor site for IVS17 is: ttttcgg$^{-1}$ G$^{+1}$GT . . . (Note: lower case letters are used to denote intron sequences upper case letters denote exon sequences. The base substitution in the −2 position of the 3' acceptor splice site is printed in boldface type).

Figure 6:
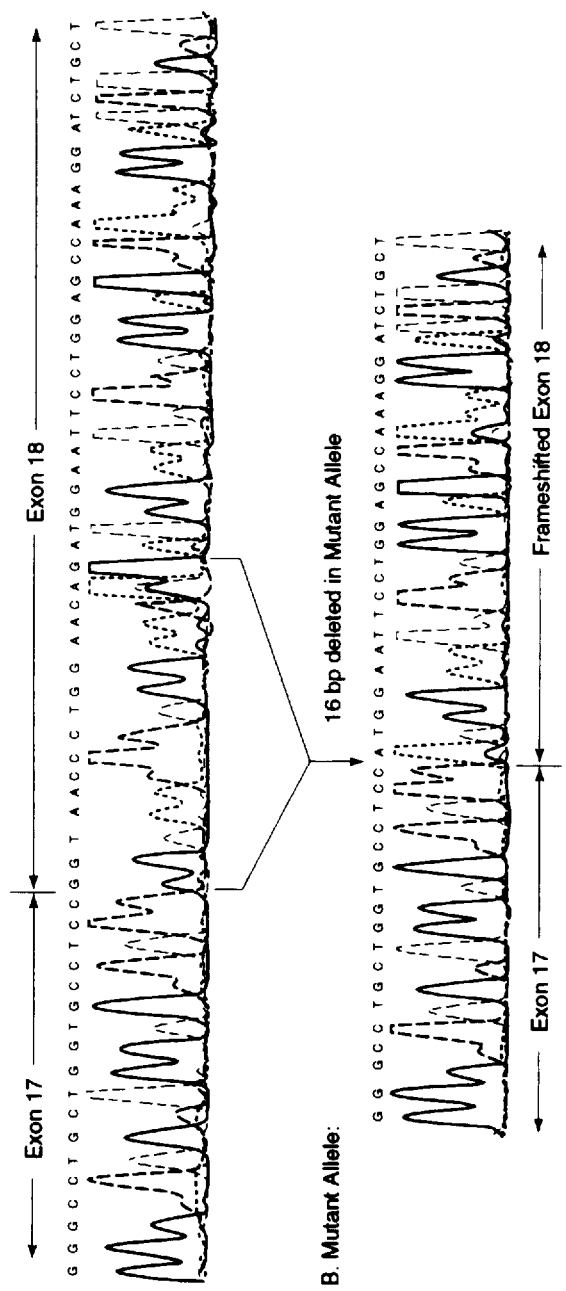

FIG. 6: Automated cycle sequencing of RT PCR products from an affected member. The primer for the RT reaction was: 3' (antisense): GAGGACCAGTTGCACCTT[SEQ ID NO:5]. The PCR primers were: 5' (sense): AAGGATTTCAAGGCAATC[SEQ ID NO:6]; 3' (antisense): GAGGACCAGTTGCACCTT[SEQ ID NO:7]. The nested PCR primers were: 5' (sense): GCTGGAAAACCTGGAAAAG[SEQ ID NO:8]; 3 (antisense): GAAGCCAGGAGCACCAGCAATGC[SEQ ID NO:9]. Automated cycle sequencing was performed using dideoxy terminator reaction chemistry for sequence analysis in the Model 373A DNA sequencing system (Applied Biosystems). Sequencing was accomplished with both sense and antisense nested PCR primers; only the sense direction is shown. Panel A: Sequencing of the RT-PCR product from the normal allele. The normal sequence was obtained. The cryptic splice site which is utilized in the mutant allele is circled. Sequence of the deleted area in the mutant allele is indicated in brackets. Panel B: Sequencing of the RT-PCR product from the mutant allele.

DETAILED DESCRIPTION OF THE INVENTION

Double-stranded nucleic acid molecules of small or intermediate size (ranging from about 15 base pairs to several thousand base pairs) generally have a rod-like shape or conformation in solution in water. Because they have the same conformation and same content of charged groups, nucleic acid molecules of different sizes in terms of number of base pairs can readily be separated by electrophoresis through any of a variety of inert gels or matrices. Under appropriate conditions, small nucleic acid molecules driven by an electrical field migrate more rapidly than large DNA molecules. The methods of the present invention is based on the principle that double-stranded homoduplexes and heteroduplexes differing only by the presence in each strand of a single base at a single site can also be separated by electrophoresis in a gel. However, the conditions for electrophoresis are critical in order to detect a difference in electrophoretic migration produced by all possible base mismatches.

Previous reports in the scientific literature demonstrated that an extra base that is not paired with a complementary base in an otherwise double-stranded DNA can change the normal rod-like shape or conformation of the molecule. For example, examination of small double-stranded DNAs of only 8 or 13 base pairs by nuclear magnetic resonance demonstrated that the presence of one extra base in one strand caused a change in conformation defined as a "bulge" in the structure. Woodson & Crothers, (1988) *Biochemistry* 27:3130–3140 and Kalnik et al., (1989) *Biochemistry* 28:294–303. Also, it was previously demonstrated that the electrophoretic migration of a DNA band can be altered by the presence of an extra base in one strand if the DNA fragment with the extra base is joined to many identical fragments to form a concatamer in which the change in conformation is exaggerated by being present many times in the same molecule. Wang & Griffith, (1991) *Biochemistry* 30:1358–1363. However, it is impractical to use nuclear magnetic resonance or concatamers of short nucleic acid fragments for the purposes of the present invention.

Figure 1A:
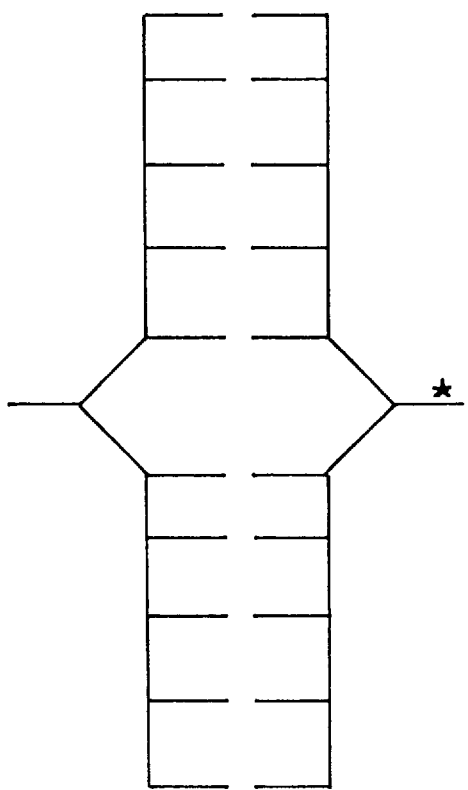
FIG. 1A is a schematic representation of the "flip" model of DNA tertiary structure resulting from a mismatched base pair.
Figure 1B:
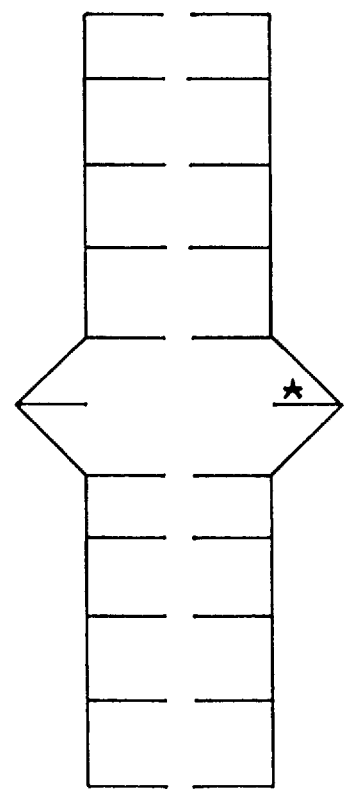
FIG. 1B is a schematic representation of the "bubble" model of DNA tertiary structure resulting from a mismatched base pair.

The present invention provides methods of differentiating homoduplexes from heteroduplexes in a sample by the selection of appropriate conditions selected to enhance the conformational change in the nucleic acid double helix which results from mismatched base pairs of heteroduplexes. Mismatched, as used herein means that a base is not base-paired with the complementary base in the complementary strand of DNA. The presence of a mismatched base pair at the same site in a double stranded nucleic acid molecule will cause rotation out from the center of the double helix ("flip model" FIG. 1A) or cause separation of the bases in the double helix ("bubble model", FIG. 1B). Thus, selection of appropriate conditions exaggerates the difference in electrophoretic mobility between the homoduplex and the heteroduplex. Such methods can be used to rapidly determine whether or not a nucleic acid fragment contains a single base mutation or other difference in base sequence from a standard sample of the same nucleic acid fragment. Such methods may be particularly useful for the detection of genetically linked diseases, among other uses.

As used herein, a standard sample is a sample of nucleic acid duplexes (comprising two complementary nucleic acid fragments) which may comprise normal, unmutated or wild type nucleic acid fragments. The standard nucleic acid sample may further be understood to have a known sequence from which a test sample is to be differentiated in terms of a base change (mutation). The nucleic acid fragments may be DNA or RNA fragments. Duplexes of the present invention may be comprised of homospecies such as DNA—DNA and RNA—RNA duplexes, or heterospecies such as DNA-RNA duplexes. Nucleic acid fragments of the present invention may range in length from about 15 to about 2000 base pairs. In preferred embodiments of the present invention, the nucleic acid fragments range in length from about 50 to about 1500 base pairs. In still more preferred embodiments of the present invention, nucleic acid fragments are 200 to about 1000 base pairs in length. "Homoduplex" as used herein refers to a duplex of nucleic acid fragments in which the two fragments are completely complementary. "Heteroduplex" as used herein refers to a duplex of nucleic acid fragments in which the two fragments are substantially complementary, thereby supporting hybridization, but where one or more base pairs are not complementary. Differentiation of heteroduplexes from homoduplexes is meant, in the normal sense of the word, to refer to the recognition of a difference which exists between the two duplexes. In this instance preferably the difference is embodied as a difference in the migration of the hetero- and homoduplexes in a polyacrylamide gel.

In accordance with some preferred embodiments of the present invention heteroduplexes and homoduplexes are generated. Samples of standard nucleic acid fragments may be commercially available or may be isolated from a subject which has been determined to have a desired characteristic. For example, a subject may have a normal collagen gene which may be used as a standard. Methods of isolating nucleic acid samples from plants and animals are known to those skilled in the art. See, for example, Sambrook, et al. *Molecular Cloning: A Laboratory Notebook* (Cold Spring Harbor Press, Cold Spring Harbor, N.Y, 1989). Standard sequences may also be prepared by automated synthesis using automated nucleic acid synthesizers which are commercially available, such as from Applied Biosystems, Inc. Samples of test nucleic acid fragments may similarly be isolated from a subject, be it a plant or animal. Thus, a nucleic acid sample from a patient suspected of carrying a collagen mutation may be isolated and screened by methods of the present invention.

A sample of wild type nucleic acid fragment (standard) and a sample of test nucleic acid fragment which is being tested for the presence of single base pair mutations or changes, may be mixed and heated under denaturing conditions so that the duplexes separate into single stranded fragments. The sample may be cooled so that the single strands re-associate into a mixture of homoduplexes and heteroduplexes. Parameters, such as time and temperature, for the dehybridization of duplexes are known to those skilled in the art as are the parameters necessary for rehybridization. For example, see Innis, et al. ed., *PCR Protocols* (Academic Press, Inc., San Diego 1990).

In some embodiments of the present invention, amplification, such as by polymerase chain reaction, may be performed on the mixture prior to heating and cooling in order to amplify the strands and facilitate detection of the duplexes. Methods of amplification are known to those skilled in the art, such as polymerase chain reaction. Innis, et al. ed., *PCR Protocols* (Academic Press, Inc., San Diego 1990).

The samples may then be analyzed by gel electrophoresis using a slightly denaturing or otherwise modified polyacrylamide gel in accordance with methods of the present invention. If there is a single base pair difference or other difference between the test sample and the standard sample, one or more bands of heteroduplexes are seen in addition to the band of homoduplexes. The bands of homoduplexes and heteroduplexes are readily detected by standard techniques for the analysis of DNA bands on gels such as staining with ethidium bromide or hybridization of the DNA in the bands with any one of a variety of different kinds of DNA probes using detection systems familiar to those skilled in the art.

Polyacrylamide gels useful in methods of the present invention may comprise from about 3% to about 20% polyacrylamide composed of a bisacrylamide:acrylamide mixture having a ratio of approximately 0:1 to about 1:32. In still more preferred embodiments of the present invention from about 5% to about 15% polyacrylamide is used for the preparation of the gel. Percentage, as used herein, refers to the weight per volume or volume per volume percent, depending upon the nature of the reagent (i.e. solid or liquid). Thus, the percent polyacrylamide is a volume per volume percent.

Polyacrylamide gels useful in methods of the present invention further comprise from about 1% to about 50% of a denaturing component comprising at least one denaturing agent selected from the group consisting of aliphatic alcohols such s methyl, ethyl, isopropyl, n-propyl, allyl, butyl, isobutyl, nd amyl alcohols and ethylene glycol; cyclic alcohols such as cyclohexyl, benzyl, phenol, and p-methyoxyphenol alcohol and inositol; alicyclic compounds such as aniline, pyridine, purine, 1,4-dioxane, butyrolactone, and aminotriazole; amides such as formamide, ethylformamide, dimethylformamide, acetamide, N-ethylacetamide, N,N-dimethylacetamide, propionamide, glycolamide, thioacetamide, valerolactam; ureas such as carbohydrazide, 1,3-dimethylurea, ethylurea, t-butylurea, thiourea, and allylthiourea; carbamates such as urethan, N-methylurethan and N-propylurethan and other compounds such as cyanoguanidine, sulfamide, glycine, acetonitrile, Tween 40 and Triton X-100. Of course other denaturing components useful in the present invention may be identified by those skilled in the art. In more preferred embodiments of the present invention from about 5% to about 30% of a denaturing component comprising at least one denaturing agent is used to prepare the gel. Most preferably about 25% denaturing component comprising at least one denaturing agent is used to prepare gels of the present invention. Of course a denaturing component may comprise more than one denaturing agent selected to optimize the mildly denaturing conditions of the polyacrylamide gel.

Polyacrylamide gels of the present invention still further comprise from about 10 mM to about 1200 mM TE buffer. From about 30 mM to about 50 mM TE buffer is used in still more preferred embodiments of the invention. TE buffer is the commonly used term for a buffer comprising EDTA and Tris-HCl having a ratio which may range from about 1 to 10 to about 1 to 50 moles EDTA to Tris-HCl. Preferably TBE (which comprises borate, Tris-HCl and EDTA) is not employed in methods of the present invention due to undesirable reactivity of borate with denaturing agents of the present invention.

From about 10 mM to about 100 mM of taurine is also used in the preparation of polyacrylamide gels of the present invention. From about 10 to about 30 mM taurine may be used in some preferred embodiments of the present invention.

The method of invention also provides a means of predicting in advance which DNA fragments have isolated high melting domains. Isolated high melting domains are regions of a nucleic acid duplex with high melting profiles, i.e. a region in which more extreme conditions are required to dehybridize the two strands of nucleic acids than are required to melt the whole molecule on average. Such isolated high melting domains can be determined from analysis of the nucleic acid base compositions of a given nucleic acid sequence. Computer programs are available to perform such analysis, such as described by Lerman and Silverstein, *Methods in Enzymology,* 155: 482–501 (1987).

Isolated high melting domains are relatively rare. Nonetheless, nucleic acid fragments in which an isolated high melting domain is present may require more extreme conditions in order to differentiate hetero- and homoduplexes so that single base pair mutants may be detected especially where the temperature for 95% helicity is greater than about 4 degrees higher than the average temperature for 95% helicity of whole DNA sequence. Accordingly, such information must be taken into account if a high-melting domain is identified within the nucleic acid sequence to be analyzed for the presence of a mutation.

Detection of a mutation or other base change in a isolated high-melting domain will be improved if conditions are changed so as to decrease the hydrophobic forces that hold bases within the interior of double-stranded nucleic acid sequence as compared to conditions useful for a nucleic acid sequence which is devoid of any isolated high melting domain. By decreasing hydrophobic forces within the molecule, the molecular forces that keep nucleic acid molecules in a rod-like conformation are decreased. Similar effects may be achieved by conditions that dehydrate the molecule or drive phosphate groups from the outside to the interior of the molecule.

One skilled in the art will be able to vary the composition of the mildly denaturing polyacrylamide gel accordingly. For example, a nucleic acid sequence in which no isolated high melting domain is present might be considered a base line. Therefore, in order to increase hydrophobicity and denaturing conditions, the concentration of denaturing agents may be increased from the conditions used at base line. Alternatively, the composition of the gel can be made more favorable for the separation of hetero- and homoduplexes by replacing a weak denaturing agent such as ethylene glycol and/or formamide by any one or more of a number of stronger denaturing agents. The strength of a given denaturing agent can be determined, such as by reference to Levine, et al., *Biochemistry,* 2:168–175 (1963) which is incorporate by reference herein in its entirety. See also, Meichior and von Hippel, (1973) *Proc. Natl. Acad. Sci. USA* 70:298–302; and Oroz and Wetmur, (1977) *Biopolymers* 16:1183–1199). Thus, it may be desirable to use one or more slightly stronger denaturing agents such as ethyl alcohol, inositol, N-ethylformamide, urea, or sulfamide, or one or more still stronger denaturing agents such as ethylurea, t-butyl alcohol, N-ethylacetamide, or urethan. Accordingly, any of a number of denaturing agents that are known to those skill in the art to promote the unfolding and dissociation of double-stranded DNA into single-stranded DNA may be used by one skilled in the art to appropriately adjust the degree of hydrophobicity and denaturing characteristics of a gel. Furthermore, the effects of these chemical reagents can be enhanced by modifying conditions such as elevating temperatures and adjusting the pH away from neutrality. Such effects may also be enhanced by addition of intercalators which intercalate into the double helix of the nucleic acid, such as ethidium bromide. Chemical reagents which dehydrate the double helix of the nucleic acid strands or which cause the phosphate groups in the molecule to rotate into the interior of the double helix may also be used to enhance the effects of the denaturing agents. Under some conditions separation can be enhanced by changing the fragments by cleavage into smaller fragments or ligation of the fragments to themselves or other molecules to create larger fragments. Such modifications can be performed readily by a routineer in the art.

Kits are also provided in accordance with methods of the present invention. For example, premade polyacrylamide gels, such as mini-gels, prepared in accordance with the parameters of the present invention may be prepared for use with methods of the present invention. Mini-gels are particularly useful for some aspects of the present invention since they are relatively inexpensive to prepare and are completely disposable. Kits of the present invention may further comprise a selected set of PCR primers for amplification of a desired gene. For example, PCR primers for amplification of COL2A1, COL7A1 and COL3A1 may be provided along with a premade polyacrylamide gel in which the degree of denaturation has been optimized for the particular gene.

The present invention will become more apparent by consideration of the following, non-limiting examples.

EXAMPLES

Example 1

Detection of Single-base Mismatches in One Sequence Context

Four variants of the filamentous phage M13 were prepared so that they had identical base sequence but for a different single base change at the same site in each variant. The M13 phage were cloned and the cloned DNA was used as a substrate for PCR using two oligonucleotide primers that generated fragments of 485 bp. The PCR products from the pairs of different variants were mixed, denatured, and renatured to generate both homoduplexes and heteroduplexes containing all eight possible single-base mismatched pairs. The DNA homoduplexes and heteroduplexes were analyzed by gel electrophoresis under conditions described below.

Figure 2:
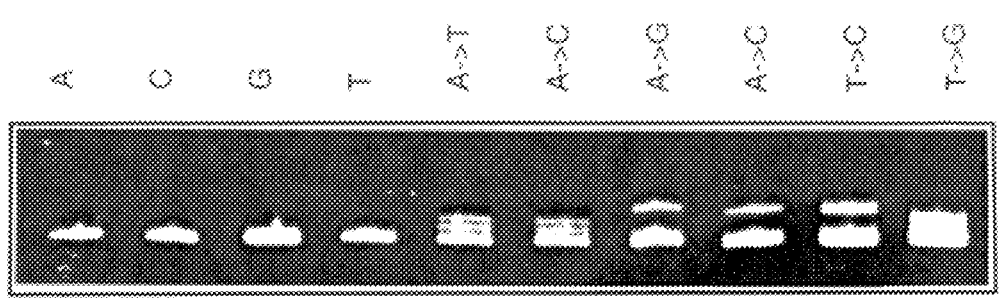
FIG. 2 is a polyacrylamide gel of PCR products from M13 templates. Lanes 1–4 show homodimers. Lanes 5–10 show heterodimers and homodimers.

The conditions for electrophoresis of the DNA samples were as follows: The gel matrix consisted of 5% polyacrylamide prepared from acrylamide and bisacrylamide in a ratio of 29:1. The solvent in which the gel was polymerized consisted of 10% of ethylene glycol, 15% formamide, 0.5 mM EDTA, 49 mM Tris-HCl and 15 mM taurine adjusted to pH 9.0. The buffer in the upper chamber of the electrophoresis apparatus consisted of 24 mM Tris-HCl, 7 mM taurine and 0.15 mM EDTA also adjusted to pH 9. The buffer in the lower chamber for electrophoresis consisted of buffer in four times the concentration of the buffer in the upper chamber. The gel was run at room temperature for 4 h at 45 watts. The gel was stained in 0.5 μg/ml ethidium bromide 0.5 μg/ml for 10 min and destained for 10 min before photography under an ultraviolet light. As indicated in FIG. 2, the DNA homoduplexes migrated as single bands. The mixture of homoduplexes and heteroduplexes migrated as two or three bands (lanes marked A→T, A→C, A→G, G→C, T→C, T→G). As indicated in Table I, all possible single-base mismatches were detected. Also, for most of the samples, the specific bands of heteroduplexes could be identified on the basis of the mismatch in the sample (except heteroduplex bands of GT, TG and GA). Two distinct bands were seen with the GG and CC mismatches, but the results did not conclusively establish which band was from which heteroduplex.

TABLE I

| Mutation in M13 | Heteroduplex Mismatched Base Pairs | Extra Band Detected |
|---|---|---|
| A → T | AA | yes |
| A → T | TT | yes |
| A → C | AG | yes |
| A → C | TC | yes |
| A → G | AC | yes |
| A → G | GT | no |
| G → C | GG | yes[a] |
| G → C | CC | no[a] |
| T → C | TG | no |
| T → C | CA | yes |
| T → G | TC | yes |
| T → G | GA | no |

[a]Identity of extra band not proven.

Example 2
Detection of Single Base Mutations Present in Human Genes

Modifications of the procedure described in Example 1 were used to detect a series of single base mutations in several human genes. One series of mutations were in the genes for several collagens: type II collagen (COL-2A1), type VII collagen (COL7A1), and type III collagen (COL3A1). A series of mutations were in the gene for the enzyme DNA topoisomerase. Another series of mutations were on exon 8 for the coagulation factor IX. Also, one mutation was in the gene for elastin.

With each of these examples, selected regions of the genes were amplified by PCR using as templates either genomic DNA extracted from cells or cloned DNA. With most of the samples, the genomic DNA was from patients who were heterozygous and therefore included one allele of the wild type (standard) sequence and another allele with a single base mutation. Therefore, the PCR products contained copies of both the wild type allele and the mutated allele. Denaturing and then renaturing the PCR products from both alleles generated both the homoduplexes and heteroduplexes needed for the analysis. With other samples, cloned DNAs were used and PCR products from the wild type and the mutated sequence were mixed, denatured and renatured to generate both homoduplexes and heteroduplexes.

Figure 3A:
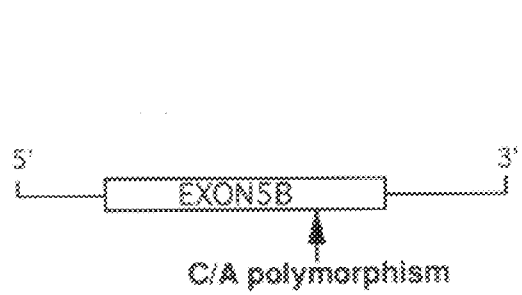
FIG. 3 is a polyacrylamide gel of PCR products for the COL2A1 Exon 5B polymorphism. Lanes 1 and 3 show heterodimers and homodimers indicating a base mismatch. Lane 2 shows a homodimer indicating base complementarity.
Figure 3B:
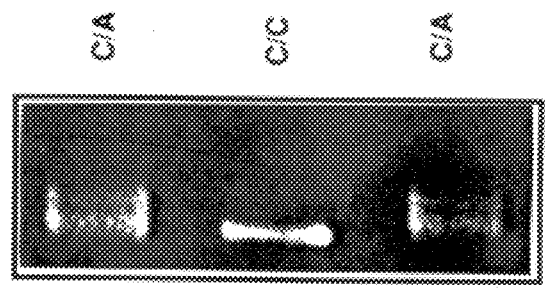

As illustrated by examples provided in FIGS. 3 and 4, the single-base mutations were readily detected by the differences in electrophoretic migrations of homoduplexes and heteroduplexes. For example, a C to A mutation in the COL2A1 gene was readily detected (lanes marked C/A in FIG. 3). Two mutations in the COL7A1 gene were readily detected (lanes marked G/A and C/T in FIG. 4). The results from assaying 78 different mutations are summarized in Table II.

TABLE II

| Gene | Single Base Changes Tested | Correct Detection | False Negative |
|---|---|---|---|
| M13 Phage | 10 | 10 | 0 |
| COL2A1 | 7 | 7 | 0 |
| COL7A1 | 8 | 8 | 0 |
| Topoisomerase | 12 | 12[a] | 0 |
| Elastin | 1 | 1 | 0 |
| Factor IX-exon 8 | 35 | 31 | 4 |
| COL3A1 | 5 | 2 | 3[b] |
| TOTAL | 78 | 71 | 7 |

[a]8% polyacrylamide gels used.
[b]In isolated high-melting domains.

Example 3
Identification of Isolated High-Melting Domains

As indicated in Example 2, Table II, 7 of the 78 single-base mutations were not detected. The sequences were analyzed with a computer program (see L. S. Lerman and K. Silverstein, (1987) *Methods in Enzymology* 155:482–501) that predicts the melting profile of the base sequences, i.e. the tendency of the sequences to unfold or melt from a double-stranded to a single-stranded conformation as the temperature of the DNA solution is raised. The computer program provides the data as the temperature at which the sequences have a 95% probability of being double-helical. The analyses demonstrated that the mutations readily detected were in domains in which the melting temperature of the domain containing the mutation was relatively close to the melting temperature of the whole molecule of double-stranded DNA. In contrast, the three mutations in the COL3A1 gene that were not detected (Table III) were in domains in which the melting temperature of the domain as considerably higher than the melting temperature of the hole molecule of DNA. Specifically, the three mutations in the COL3A1 gene that gave false negative results were in isolated domains in which the temperature for 95% helicity was 6.7 to 10.0 degrees higher than the average temperature for 95% helicity of whole DNA sequence of the PCR product (see column marked (δT) in Table III). δT can be calculated to be [temperature for 95% helicity of the mutation site—average temperature for 95% helicity for the entire nucleic acid sequence]. In contrast, an easily detected mutation in the COL3A1 gene was in an isolated domain where the temperature for 95% helicity was on 3.4 degrees higher than the average temperature for 95% helicity of the entire DNA sequence of the PCR product. Thus, a DNA sequence to be analyzed can be processed by a computer program to determine whether or not the sequence contains an isolated high-melting domain that is unusually stable relative to the rest of the sequence. If such an isolated high-melting domain is not found, the method has a high probability of detecting all single base mismatches. If such an isolated high-melting domain is found, the conditions of the method must be adjusted to detect mismatches in the particular isolated region.

TABLE III

TEMPERATURE FOR 95% HELICITY

| MUTATION | AVERAGE | MUTATION SITE | δT | DETECTION |
|---|---|---|---|---|
| G/A | 67.4 | 70.8 | 3.4 | + |
| C/T | 64.5 | 72.2 | 7.7 | − |
| C/A | 65.4 | 75.4 | 10.0 | − |
| G/A | 68.5 | 75.2 | 6.7 | − |

Example 4
Comparison of two formulations for Conformation-Sensitive Gel Electrophoresis (CSGE)

Formulation I: Prior to electrophoresis, 4 ml of each PCR product was mixed with 4 ml of 20% ethylene glycol/30% formamide containing 0.025% (wt/vol) each of xylene cyanol FF nd bromophenol blue. A standard DNA sequencing gel apparatus as used with 37.5 by 45 cm glass plates and a 36-sample comb. A 1 mm thick gel was prepared with 6% polyacrylamide and a 29:1 ratio of acrylamide to bis-acrylamide (BIS), 10% ethylene glycol (Sigma Chemicals, St. Louis, Mo.), and 15% formamide (Gibco BRL, Bethesda, Md.) in 45 mM Tris HCI/15 mM taurine/0.5 mM EDTA buffer at pH 9.0 (0.5 X-TTE; U.S. Biochemical Corp., Cleveland, Ohio). The electrode buffers were 0.25 X TTE in the upper chamber and 1X-TTE in the lower chamber. The gel was pre-electrophoresed at 750 volts until the current became constant and the samples were then electrophoresed at 400 volts overnight at room temperature. Monitoring with embedded temperature-sensitive liquid crystal strips (AT Biochemicals, Malvern, Pa.) indicated that the temperature was less than 35° C. inside the gel. After electrophoresis, one glass plate was removed and the gel on the second glass place was stained with 1 mg/ml ethidium bromide for 6 minutes followed by destaining for 12 minutes. The bands were visualized with a handheld UV torch. The relevant section of the gel was cut, transferred with a piece of blotting paper to a transilluminator, and released from the paper by wetting with water. The gel was then photographed under standard conditions.

Formulation II: Improved conditions for CSGE. The gel described in Formulation above is useful for many applications, but is fragile and therefore frequently difficult to manipulate. The cross-linker bis-acrlyloylpiperazine (BAP) was therefore used in place of bis-acrylamide (BIS), since BAP improves the resolutions of protein separation and also enhances the physical strength of polyacrylamide gels. PCR products were analyzed using this new formulation which ranged in length from 150 to 936 bp. The best results were obtained using a 10% polyacrylamide gel prepared with 99 parts of acrylamide to 1 part of BAP although formulations of about 90 parts of acrylamide to about 10 parts of bis-acrolylpiperazine or about 95 parts of acrylamide to about 5 parts of bis-acrolylpiperazine may also be useful. The gel may comprise other ratios of acry-lamide to bis-acrolylpiperazine depending upon the types of nucleic acids to be resolved as will become apparent to those skilled in the art. Gels so made are firmer and easier to manipulate. In addition, the differences in mobility between heteroduplexes and homoduplexes were generally greater in this formulation than when BIS was used. The presence of ethylene glycol and formamide was not essential to dem-onstrate the differential migration of most mismatches, but these compounds were still helpful for detection of some mismatches, particularly A:A and C:T mismatches.

Example 5
Use of CSGE to detect an $A^{-2} \rightarrow G$ transition at the 3' acceptor splice site of IVS17 which characterizes the COL2A1 gene mutation in the original stickler syndrome kindred.

Hereditary progressive arthro-ophthalmopathy, or "Stickler Syndrome", is an autosomal dominant osteochondrod-ysplasia characterized by a variety of ocular and skeletal anomalies which frequently lead to retinal detachment and precocious osteoarthritis. A variety of mutations in the COL2A1 gene have been identified in "Stickler' families; in most cases studied thus far, the consequence of mutation is the premature generation of a stop codon. In the present study, the characterization of a COL2AI gene mutation in the original kindred described by Stickler et al. is described (Stickler et al., 1965, Hereditary Progressive Arthro-Ophthalmopathy. Mayo Clinic Proceedings 40:(6) :433–455).

Using CSGE and the Formulation II conditions described above, it was possible to screen for mutations in the entire COL2A1 gene in an affected member from the kindred. A prominent heteroduplex species was noted in the PCR product from a region of the gene including exons 17 to 20. Direct sequencing of PCR amplified genomic DNA resulted in the identification of a base substitution at the $A^{-2}$ position of the 3' splice acceptor site of IVS17. Sequencing of DNA from affected and unaffected family members confirmed that the mutation segregated with the disease phenotype. Reverse transcriptase-PCR (RT-PCR) analysis of poly A+ RNA demonstrated that the mutant allele utilized a cryptic splice site in exon 18 of the gene eliminating 16 bp at the start of exon 18. This frameshift eventually results in a premature termination codon.

CSGE was used to screen for mutations in all 54 exons of the COL-2A1 gene in an affected member from the kindred. Table IV summarizes the results of these analyses.

TABLE IV

| Region containing heteroduplex species | Polymorphism detected | Mutation detected |
|---|---|---|
| 17–20 | | $A^{-2} \rightarrow G$ (IVS17) |
| 32–33 | −22 exon 33 (g → a) | |
| 34–35 | $CTG^{587} \rightarrow CTT$ | |
| 38 | nd | | nd: not detected

Figure 5:
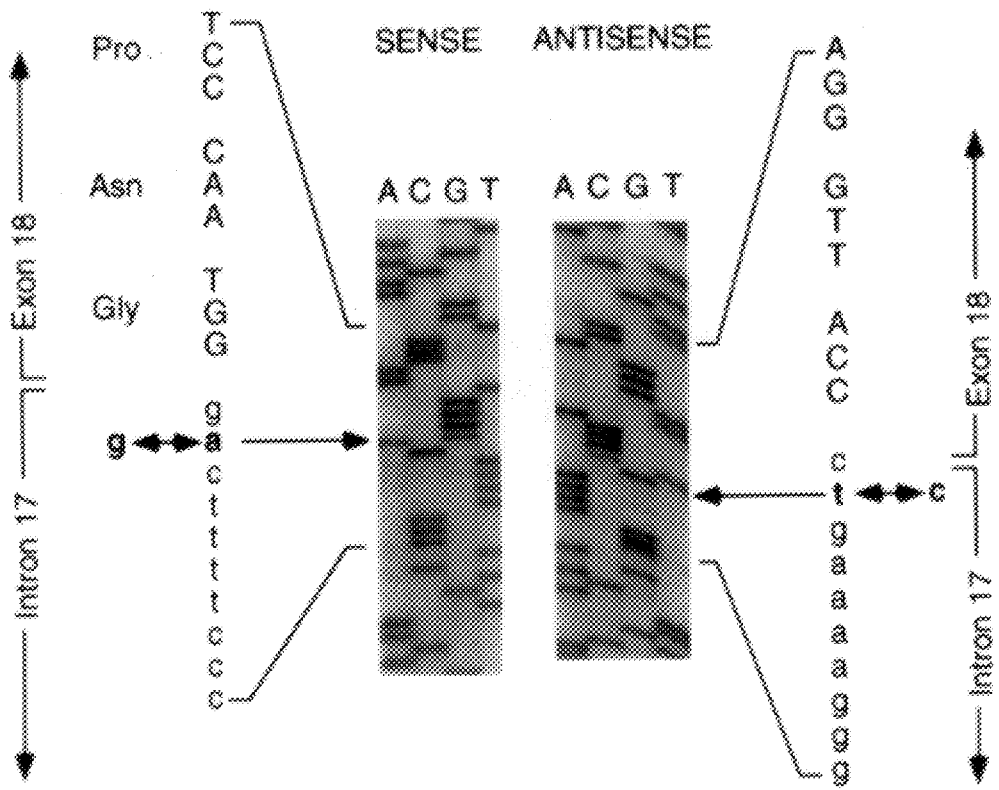
FIG. 5 is a photograph of a gel depicting manual dideoxynucleotide sequence analysis of a genomic DNA PCR product showing the IVS17 splice site mutation in DNA obtained from a Stickler syndrome patient. The region of base substitution at the IVS17 splice acceptor site is indicated by an arrow. The PCR primers for exons 17–19 are: 5' (sense): agtgctgtcgttgcagctgg[SEQ ID NO:1]; 3' (antisense): gactccagagatgtcagtggaac[SEQ ID NO:2]. The sequencing primers are: 5' (sense): tggatctggatcctggag[SEQ ID NO:3]; 3' (antisense): aggcaggactgggctctc[SEQ ID NO:4]. Direct sequencing of the genomic DNA PCR product allows visualization of both normal and mutant alleles. Sense and antisense sequencing results ere shown.

Four regions exhibited heteroduplex species; the exons within these regions, and the regions 50 bp upstream and downstream of each exon boundary, were subjected to manual dideoxynucleotide and automated cycle sequencing analysis. Two of the four species were found to be the result of neutral polymorphisms. The sequence variation giving rise to one heteroduplex species was not identified; it probably resided well into the intron beyond the region that was subjected to sequence analysis. However, when direct sequencing of PCR amplified genomic DNA from an affected member was undertaken for the axon 17–20 area of the gene, a base substitution was identified in the A-2 position of the 3' acceptor splice site of IVS17 (Table 1 and FIG. 1). The mutation was confirmed by antisense sequencing of the gene at this position (FIG. 5) and by restriction enzyme digestion. DNA from several affected and unaffected family members was subsequently PCR amplified and analyzed for the base substitution. Results of these analyses confirmed that the mutation was present in affected members only. The mutation was absent in DNA from 114 normal, unrelated control subjects.

To determine if the mutation affected the splicing of COL2A1 mRNA transcripts, cDNA from the proband was generated by RT-PCR of lymphoblast poly A+ RNA (Chan et al., 1991, J. Biol. Chem. 266:12487–12494) . The reverse transcriptase reaction was primed with the antisense downstream primer positioned at the 3 end of axon 19. PCR amplification was completed by using outside primers located in exons 8 and 19, followed by a nested amplification with primers located in exons 10 and 19. The RT-PCR reaction products were subjected to automated cycle sequencing using the sense and antisense nested PCR primers to prime the sequencing reactions. The normal allele gave rise to a transcript that was of the expected size and sequence (FIG. 5A). However, the mutant allele gave rise to a shortened transcript as a result of the inability of the splice donor in intron 17 to utilize the mutant acceptor splice site. Sequence analysis demonstrated that a cryptic splice site in exon 18 was utilized as the new splice acceptor in the mutant allele, resulting in the deletion of 16 bp from the start of exon 18 (FIG. 6B). This frameshift deletion eventually resulted in the generation of a premature stop codon 645 bp downstream from the inappropriate splice site.

What is claimed is:

1. A method for detecting one or more base pair mutations in a nucleic acid sequence by differentiating by conformation heteroduplexes from homoduplexes in a sample comprising the steps of:

providing a polyacrylamide gel for gel electrophoresis comprising from about 3% to about 20% polyacrylamide, from about 1% to about 50% of at least one denaturing agent selected from the group consisting of aliphatic alcohols, cyclic alcohols, alicyclic compounds, amides, ureas, and carbamates, wherein said denaturing agent is selected to enhance resolution of homoduplexes and heteroduplexes in said gel; from about 10 mM to about 100 mM TE buffer, said TE buffer being free of borate; and from about 10 mM to about 100 mM taurine;

generating homoduplexes and heteroduplexes in a sample; and performing gel electrophoresis on said sample using said polyacrylamide gel, whereby heteroduplexes will migrate more slowly in said gel than homoduplexes thereby indicating a nucleic acid sequence having one or more base pair mutations.

2. The method of claim 1 wherein said polyacrylamide gel comprises from about 5% to about 30% of said at least one denaturing agent.

3. The method of claim 2 wherein said polyacrylamide gel comprises 10% ethylene glycol and 15% formamide.

4. The method of claim 1, wherein said polyacrylamide comprises a mixture of acrylamide and bis-acryloylpiperazine.

5. The method of claim 4, wherein said polyacrylamide comprises a mixture of acrylamide and bis-acryloylpiperazine at a ratio of 90 parts acrylamide to 10 parts of bis-acryloylpiperazine.

6. The method of claim 4, wherein said polyacrylamide comprises a mixture of acrylamide and bis-acryloylpiperazine at a ratio of 95 parts acrylamide to 5 parts of bis-acryloylpiperazine.

7. The method of claim 4, wherein said polyacrylamide comprises a mixture of acrylamide and bis-acryloylpiperazine at a ratio of 99 parts acrylamide to 1 part of bis-acryloylpiperazine.

8. A method for detecting one or more base pair mutations in a nucleic acid sequence by differentiating by conformation heteroduplexes from homoduplexes in a sample comprising the steps of:

a) generating a sample of homoduplexes;

b) analyzing said sample of homoduplexes for at least one isolated high melting domain;

c) providing a polyacrylamide gel for gel electrophoresis comprising from about 3% to about 20% polyacrylamide, from about 1% to about 50% of a denaturing component comprising at least one denaturing agent selected from the group consisting of aliphatic alcohols, cyclic alcohols, alicyclic compounds, amides, ureas, and carbamates, wherein said denaturing component is selected to enhance resolution of homoduplexes and heteroduplexes in said gel; from about 10 mM to about 100 mM TE buffer, said TE buffer being free of borate; and from about 10 mM to about 100 mM taurine, the concentration of said denaturing agent being adjusted to compensate for any isolated high melting domains identified in step b;

d) generating a sample of homoduplexes and heteroduplexes; and e) performing gel electrophoresis on said sample of homoduplexes and heteroduplexes using said polyacrylamide gel, whereby heteroduplexes migrate more slowly in said gel than homoduplexes, thereby indicating a nucleic acid sequence having one or more base pair mutations.

9. The method of claim 8 wherein said polyacrylamide gel comprises from about 5% to about 30% of said denaturing component.

10. The method of claim 9 wherein the denaturing component comprises 10% ethylene glycol and 15% formamide.

11. The method of claim 9 wherein an isolated high melting domain is identified in which δT is greater than about 4° C., and the denaturing agent comprises 25% n-propyl alcohol.

12. The method of claim 8, wherein said polyacrylamide comprises a mixture of acrylamide and bis-acryloylpiperazine.

13. The method of claim 8, wherein said polyacrylamide comprises a mixture of acrylamide and bis-acryloylpiperazine at a ratio of 90 parts acrylamide to 10 parts of bis-acryloylpiperazine.

14. The method of claim 8, wherein said polyacrylamide comprises a mixture of acrylamide and bis-acryloylpiperazine at a ratio of 95 parts acrylamide to 5 parts of bis-acryloylpiperazine.

15. The method of claim 8, wherein said polyacrylamide comprises a mixture of acrylamide and bis-acryloylpiperazine at a ratio of 99 parts acrylamide to 1 part of bis-acryloylpiperazine.

16. A kit comprising a polyacrylamide gel comprising from about 3% to about 20% of a mixture of acrylamide and bis-acryloylpiperazine, from about 1% to about 50% of a denaturing component comprising at least one denaturing agent selected from the group consisting of aliphatic alcohols, cyclic alcohols, alicyclic compounds, amides, ureas, and carbamates; from about 10 mM to about 100 mM TE buffer, said TE buffer being free of borate; and from about 10 mM to about 100 mM taurine; and PCR primers for a desired gene.

17. The kit of claim 16, wherein said polyacrylamide comprises a mixture of acrylamide and bis-acryloylpiperazine at a ratio of 90 parts acrylamide to 10 parts of bis-acryloylpiperazine.

18. The kit of claim 16, wherein said polyacrylamide comprises a mixture of acrylamide and bis-acryloylpiperazine at a ratio of 95 parts acrylamide to 5 parts of bis-acryloylpiperazine.

19. The kit of claim 16, wherein said polyacrylamide comprises a mixture of acrylamide and bis-acryloylpiperazine at a ratio of 99 parts acrylamide to 1 part of bis-acryloylpiperazine.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGTGCTGTCG TTGCAGCTGG                    20

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GACTCCAGAG ATGTCAGTGG AAC                    23

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TGGATCTGGA TCCTGGAG                    18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGGCAGGACT GGGCTCTC                                                                                          18

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GAGGACCAGT TGCACCTT                                                                                          18

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AAGGATTTCA AGGCAATC                                                                                          18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GAGGACCAGT TGCACCTT                                                                                          18

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GCTGGAAAAC CTGGAAAAG                                                                                         19

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GAAGCCAGGA GCACCAGCAA TGC                                                                                    23